United States Patent
Vavelin et al.

(10) Patent No.: US 10,658,745 B2
(45) Date of Patent: May 19, 2020

(54) IMPLANTABLE MEDICAL DEVICE WITH MULTI-BAND LOOP ANTENNA

(71) Applicant: Cochlear Limited, Macquarie University, NSW (AU)

(72) Inventors: Guilhem Vavelin, Nice (FR); Gauthier Jodin, Antibes (FR)

(73) Assignee: Cochlear Limited, Macquarie University, NSW (AU)

( * ) Notice: Subject to any disclaimer, the term of this patent is extended or adjusted under 35 U.S.C. 154(b) by 257 days.

(21) Appl. No.: 15/697,618

(22) Filed: Sep. 7, 2017

(65) Prior Publication Data
US 2019/0074585 A1 Mar. 7, 2019

(51) Int. Cl.
| | | |
|---|---|---|
| H01Q 1/52 | (2006.01) |
| H01Q 7/00 | (2006.01) |
| A61N 1/372 | (2006.01) |
| H01Q 5/50 | (2015.01) |
| H01Q 1/27 | (2006.01) |
| H04B 5/00 | (2006.01) |
| H04B 1/00 | (2006.01) |
| A61N 1/36 | (2006.01) |
| H04B 1/3805 | (2015.01) |

(52) U.S. Cl.
CPC .......... *H01Q 1/52* (2013.01); *A61N 1/37229* (2013.01); *H01Q 1/273* (2013.01); *H01Q 5/50* (2015.01); *H01Q 7/00* (2013.01); *H04B 1/00* (2013.01); *H04B 5/0081* (2013.01); *A61N 1/36038* (2017.08); *H04B 1/3805* (2013.01)

(58) Field of Classification Search
CPC .............................. H01A 1/52; A61N 1/37229
USPC .......................................................... 607/60
See application file for complete search history.

(56) References Cited

U.S. PATENT DOCUMENTS

| | | | |
|---|---|---|---|
| 8,369,959 B2 | 2/2013 | Meskens | |
| 9,522,268 B2 | 12/2016 | Dhanasingh et al. | |
| 2008/0300658 A1* | 12/2008 | Meskens | A61N 1/08 607/60 |
| 2016/0213925 A1 | 7/2016 | Karunasiri | |

FOREIGN PATENT DOCUMENTS

| | | |
|---|---|---|
| CN | 101669250 A | 3/2010 |
| EP | 2052758 A1 | 4/2009 |
| JP | 5655159 B2 | 1/2015 |

OTHER PUBLICATIONS

International Search Report and Written Opinion in corresponding International Application No. PCT/IB2018/056606, dated Mar. 21, 2019, 8 pages.

* cited by examiner

*Primary Examiner* — Nadia A Mahmood
(74) *Attorney, Agent, or Firm* — Edell, Shapiro & Finnan, LLC (57) ABSTRACT

Embodiments presented herein are generally directed to implantable medical devices that are configured for both near-field communication and far-field communication via the same implantable loop antenna. More specifically, the implantable medical devices include implant electronics that are independently coupled to the loop antenna via a transformer and an isolation coupler. The transformer is configured to provide near-field signals received at the loop antenna to the implant electronics, while the isolation coupler is configured to provide far-field signals received at the loop antenna to the implant electronics.

27 Claims, 5 Drawing Sheets

IMPLANTABLE MEDICAL DEVICE WITH MULTI-BAND LOOP ANTENNA

BACKGROUND

Field of the Invention

The present invention relates generally to implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect an implantable medical device is provided. The implantable medical device comprises: a multi-band loop antenna; implant electronics; a near-field receiver circuit coupled to the loop antenna and the implant electronics and configured to receive, via the loop antenna, near-field signals from one or more devices positioned external to a body of a recipient and to provide the near-field signals to the implant electronics; and a far-field receiver circuit coupled to the loop antenna and the implant electronics and configured to receive, via the loop antenna, far-field signals from at least one device positioned external to the body of the recipient and to provide the far-field signals to the implant electronics.

In another aspect an implantable medical device is provided. The implantable medical device comprises: implant electronics; an implantable loop antenna; a transformer having a primary side connected to the loop antenna and a secondary side connected to the implant electronics, wherein the transformer is configured to receive, via the loop antenna, radio-frequency (RF) signals in the near-field; and an isolation coupler having a primary side connected to the implantable loop antenna and a second side connected to the implant electronics, wherein the isolation coupler is configured to receive, via the loop antenna, RF signals in the far-field, wherein the transformer and the isolation coupler are connected in parallel with one another.

In another aspect an implantable medical device is provided. The implantable medical device comprises: implant electronics; an implantable loop antenna configured to receive both near-field radio-frequency (RF) signals and far-field RF signals from one or more devices positioned external to a body of a recipient; a transformer disposed between the implant electronics and the loop antenna and configured to provide the near-field RF signals to the implant electronics; an isolation coupler disposed between the implant electronics and the loop antenna and configured to provide the far-field RF signals to the implant electronics; and first and second capacitors connected in series with a primary side of the isolation coupler, and wherein the first and second capacitors are disposed on opposing sides of the primary side of the isolation coupler.

In another aspect an implantable medical device is provided. The implantable medical device comprises: a loop antenna; a near-field receiver circuit coupled to the loop antenna and configured to receive, via the loop antenna, near-field signals from one or more devices positioned external to a body of a recipient; and a far-field receiver circuit coupled to the loop antenna and configured to receive, via the loop antenna, far-field signals from at least one device positioned external to the body of the recipient, wherein the near-field receiver circuit and the far-field receiver circuit are configured to operate in differential mode directly from the loop antenna to receive both the near-field signals and the far-field signals, respectively.

BRIEF DESCRIPTION OF THE DRAWINGS

Embodiments of the present invention are described herein in conjunction with the accompanying drawings, in which.

DETAILED DESCRIPTION

Embodiments presented herein are generally directed to implantable medical devices that are configured for both near-field communication and far-field communication via the same implantable loop antenna. More specifically, the implantable medical devices include implant electronics that are independently coupled to the loop antenna via a transformer and an isolation coupler. The transformer is configured to provide near-field data and/or power signals (generally and collectively referred to herein as "near-field signals") received at the loop antenna to the implant electronics, while the isolation coupler is configured to provide far-field data signals ("far-field signals") received at the loop antenna to the implant electronics.

There are a number of different types of implantable medical devices in which embodiments presented herein may be implemented. However, merely for ease of illustration, the techniques presented herein are primarily described with reference to one type of implantable medical device, namely a cochlear implant. It is to be appreciated that the techniques presented herein may be used in any other partially or fully implantable medical device now known or later developed, including other auditory prostheses, such as auditory brainstem stimulators, electro-acoustic hearing prostheses, middle ear prostheses, direct cochlear stimulators, bimodal hearing prostheses, etc. and/or other types of medical devices, such as pain relief implants, pacemakers, etc.

Figure 1:
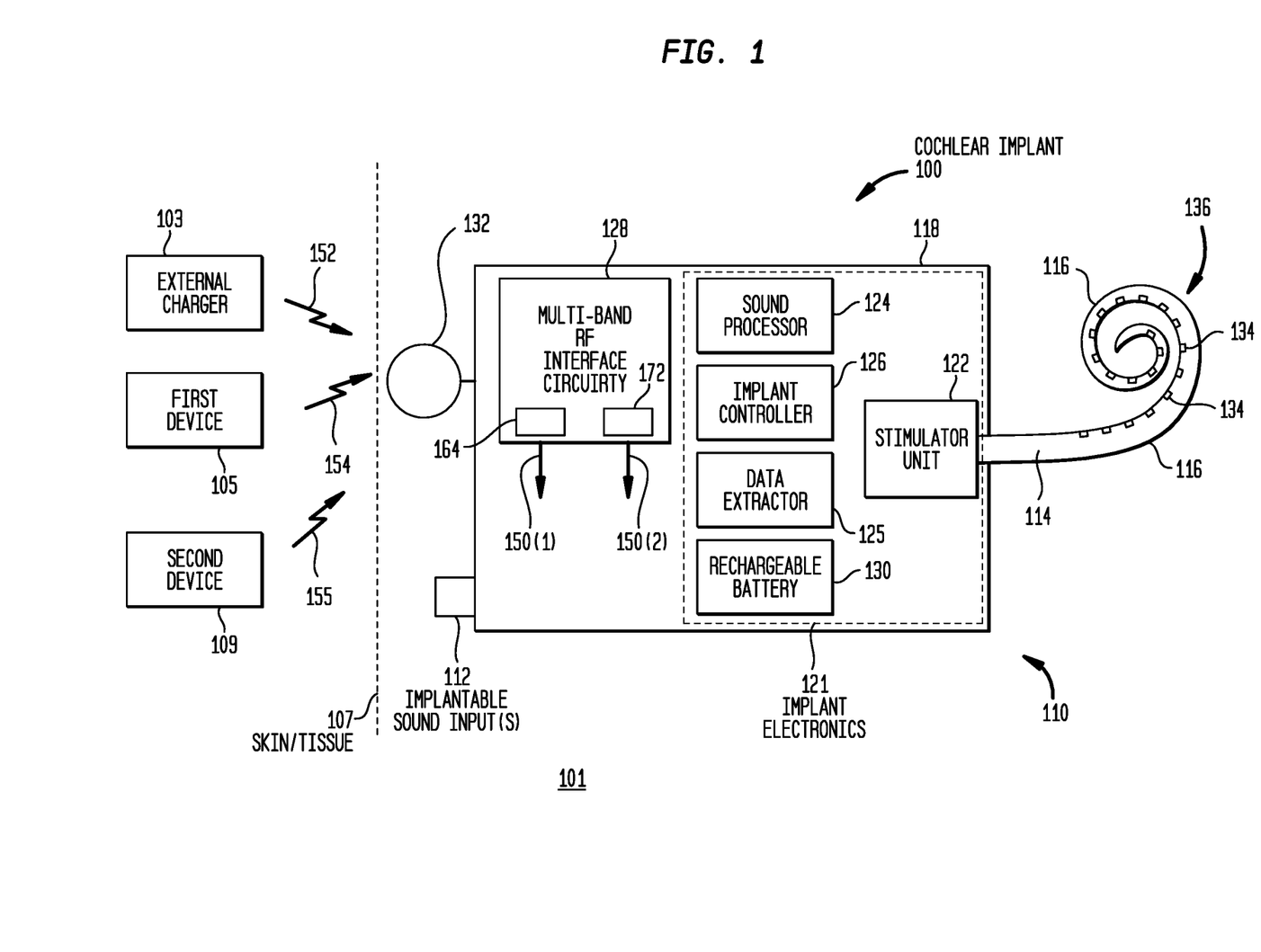
FIG. 1 is a block diagram illustrating a cochlear implant system, in accordance with certain embodiments presented herein.

FIG. 1 is block diagram of an exemplary cochlear implant system 101 in which embodiments presented herein are implemented. The cochlear implant system 101 comprises a cochlear implant 100, an external charging device (external charger) 103, a first external device 105, and a second external device 109. As described further below, the external charger 103 and the first external device 105 are devices configured for near-field communication, while the second external device 109 is a device configured for far-field communication.

In general, the electromagnetic field surrounding a transmitting antenna can be broken into a near-field region/portion (the near-field) and a far-field region (the far-field). The boundary between the two regions is only generally defined and it depends on the dominant wavelength (λ) emitted by the antenna. The near-field and the far-field have different energies. The near-field is primarily magnetic in nature, while the far-field has both electric and magnetic components. Therefore, as used herein, near-field communication refers to short-range wireless connectivity that uses magnetic field induction to enable power and/or data communication between devices that are in close proximity to one another. In contrast, far-field communication refers to long-range wireless connectivity in the electromagnetic field region dominated by electric or magnetic fields with electric dipole characteristics.

In the example arrangement of FIG. 1, cochlear implant 100 is a totally implantable cochlear implant where all components of the cochlear implant are configured to be implanted under the skin/tissue 107 of a recipient. Because all components are implantable, cochlear implant 100 operates, for at least a finite period of time, without the presence of any external devices/components, such as external charger 103, external device 105, and/or external device 109.

Cochlear implant 100 includes an implant body (main module) 110, a lead region 114, and an elongate intra-cochlear stimulating assembly 116. The implant body 110 generally comprises a hermetically-sealed housing 118 in which one or more implantable sound inputs 112, multi-band radio frequency (RF) interface circuitry 128 and implant electronics 121 are located. The implant electronics 121 include, among other elements, a stimulator unit (stimulation electronics) 122, one or more processors, such as a sound processor 124 and a data extractor component or data processor 125, an implant controller 126 (i.e., battery and power management component or battery processor), and a rechargeable battery 130. The one or more implantable sound inputs 112 may comprise, for example, one or more microphones, accelerometers, telecoils, etc.

The implant body 110 also includes an implantable multi-band loop (coil) antenna 132 that is located external to the housing 118. The multi-band loop antenna 132 is electrically connected to the multi-band RF interface circuitry 128 within the housing 118 via a hermetic feedthrough (not shown in FIG. 1). Multi-band loop antenna 132 is a wire antenna coil comprised of multiple turns of electrically insulated single-strand or multi-strand platinum or gold wire. The electrical insulation of multi-band loop antenna 132 is provided by a flexible molding (e.g., silicone molding), which is not shown in FIG. 1. In certain arrangements, a permanent magnet is fixed relative to the multi-band loop antenna 132. The permanent magnet helps to retain and align an external component by interacting with another magnet in an external device.

Elongate stimulating assembly 116 is configured to be at least partially implanted in the recipient's cochlea (not shown) and includes a plurality of longitudinally spaced intra-cochlear electrical stimulating contacts (electrodes) 134 that collectively form a contact array 136 for delivery of electrical stimulation (current) to the recipient's cochlea. Stimulating assembly 116 extends through an opening in the cochlea (e.g., cochleostomy, the round window, etc.) and has a proximal end connected to the stimulator unit 122 via the lead region 114 and a hermetic feedthrough (not shown in FIG. 1). Lead region 114 includes one or more conductors (wires) that electrically couple the electrodes 134 to the stimulator unit 122.

The one or more implantable sound inputs 112 are configured to detect/receive input sound signals that are provided to the sound processor 124. The sound processor 124 is configured to execute sound processing and coding to convert the received sound signals into output signals for use by the stimulator unit 122 in delivering electrical stimulation (current) to the recipient via electrodes 134. In this way, cochlear implant 100 electrically stimulates the recipient's auditory nerve cells, bypassing absent or defective hair cells that normally transduce acoustic vibrations into neural activity, in a manner that causes the recipient to perceive one or more components of the received sound signals.

Although cochlear implant 100 is totally implantable and able to operate without the presence of any external devices, there are times when the presence of one or more external devices are useful. As such, in the example of FIG. 1, the cochlear implant 100 is able to operate with external charger 103, first external device 105, and/or second external device 109. In general, the external charger 103 is configured to deliver charging power to the cochlear implant 100 via a communication link 152, while the device 105 is configured to send data to, possibly exchange data with, and/or possibly send power to, the cochlear implant 100 via a communication link 154. The second device 109 is configured to send data to, and possibly exchange data with, the cochlear implant 100 via a communication link 155. As noted above, the external charger 103 and the first data device 105 are devices configured for near-field communication. The signals sent via communication links 154 and 152 are magnetic induction power and/or data signals sent on/at one or more frequencies in the near-field. Also as noted, the second device 109 is a device configured for far-field communication. The signals sent via communication link 155 are data signals sent at one or more frequencies within the far-field. That is, the communication links 152 and 154 are near-field wireless communication links, while communication link 155 is a far-field wireless communication link.

The external charger 103 and the device 105 may each have a number of different forms. For example, the external charger 103 may comprise a headpiece coil wired to a battery pack, a headpiece power charger in the shape of a button, a charging headband, a pillow charger, etc. The device 105 may comprise, for example, a behind-the-ear (BTE) processor, an off-the-ear headpiece (i.e., a button processor), etc. The device 109 may comprise, for example, a remote control unit, a fitting system, a computing device (e.g., mobile phone, tablet computer, etc.), etc. It is to be appreciated that these examples are illustrative and that an implantable medical device in accordance with embodiments presented herein may communicate with a number of different types of external devices in both the near-field and the far-field.

As noted above, the cochlear implant 100 comprises the multi-band loop antenna 132 and that the multi-band RF interface circuitry 128. The multi-band RF interface circuitry 128 is configured such that the multi-band loop antenna 132 may be used to receive both near-field signals and far-field signals, potentially at the same time. Stated differently, the multi-band RF interface circuitry 128 enables the multi-band loop antenna 132 to either receive the charging power from the external charger 103 or receive power and/or data from first device 105, as well as receive data from second device 109. As a result, the multi-band RF interface circuitry 128 is configured to generate two outputs, shown in FIG. 1 as output 150(1) and output 150(2) that can each be provided to the implant electronics 121. Output 150(1) represents received near-field signals (i.e., signals received from the external charger 102 via inductive link 152 or signals received from the first device 105 via inductive link 154) and, as such, is sometimes referred to herein as a "near-field output." Output 150(2) represents received far-field signals (i.e., signals received from the second data device 109 via link 155) and, as such, is sometimes referred to herein as a "far-field output." As described elsewhere herein, the arrangement of the multi-band RF interface circuitry 128 enables the cochlear implant to generate near-field output 150(1) and far-field output 150(2) simultaneously (i.e., the multi-band loop antenna 132 may operate to simultaneously receive both near-field and far-field signals from different external devices).

The near-field and the far-field signals may each be sent at a number of different frequencies. For example, the near-field output 150(1) may comprise signals at approximately 5 Megahertz (MHz), at approximately 6.78 MHz, at approximately 13.56 MHz, at approximately 27.12 MHz, etc. The far-field output 150(2) may comprise signals above 15 MHz, more preferably well above 50 MHz (e.g. on the order of a few Gigahertz (GHz)). For example, the far-field output 150(2) may be signals in the very high frequency (VHF) range, signals in the ultra high frequency (UHF) range, or a higher frequency range. For ease of illustration, certain embodiments presented herein will be primarily described with reference to use of the multi-band loop antenna 132 and the multi-band RF interface circuitry 128 to receive signals at specific frequencies, namely at approximately 6.78 MHz via inductive link 152, approximately 5 MHz via inductive link 154, and approximately 2.4 GHz via link 155. However, it is to be appreciated that these specific frequencies are illustrative and that the techniques presented herein may be used with other circuitry configured to receive different frequencies.

In certain embodiments, the multi-band loop antenna 132 and the multi-band RF interface circuitry 128 may be configured to support a combined power and data transfer, where the data transfer may be bi-directional, at one or more frequencies. For example, while operating at the 5 MHz frequency, power and data can be modulated with one another (e.g., using on-off-keying (OOK)) or separated from one another and interleaved (e.g., time division multiple access (TDMA)) on inductive link 154. As such, the near-field output 150(1) may comprise data signals, power signals, modulated data and power, etc.

In the embodiments of FIG. 1, the multi-band loop antenna 132 operates as a "loop" antenna while receiving/ transmitting both near-field and far-field signals. As described further below, this is enabled by a transformer 164 to receive near-field signals detected at the antenna 132 and an isolation coupling circuit (isolation coupler) 172 to receive far-field signals detected at the antenna 132. As used herein, a "loop" antenna refers to a closed circuit arrangement which, when used with another loop (e.g., operating as a coupler or a transformer without a magnetic core), allows the use of radio frequency (RF) signals to generate a differential output (whereas, in contrast, a single ended antenna uses common ground to close the loop).

In accordance with embodiments presented herein, the operation of multi-band loop antenna 132 as a loop antenna to receive both near-field and far-field signals maintains a strong RF signal level and isolates the implant electronics 121 from the antenna. Moreover, the differential output may improve the sensitivity of the coil and enable a better impedance matching by precisely controlling the differential output impedance.

Figure 2:
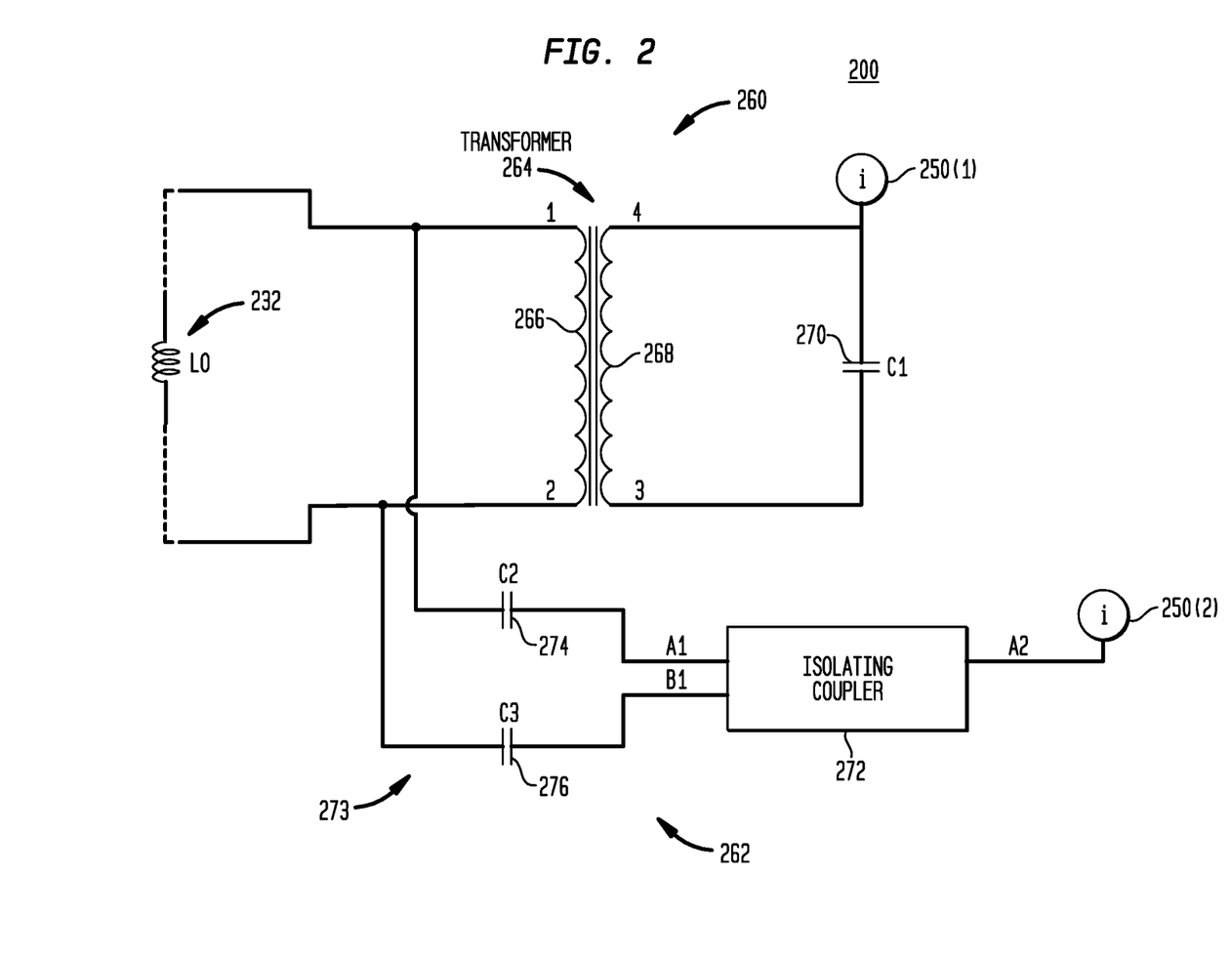
FIG. 2 is a schematic diagram illustrating a portion of a cochlear implant, in accordance with certain embodiments presented herein.

FIG. 2 is schematic diagram illustrating one example arrangement for a multi-band loop antenna and multi-band RF interface circuitry in an implantable medical device, such as cochlear implant 100, in accordance with embodiments presented herein. More specifically, shown is a portion of a cochlear implant 200 that includes, among other elements, a multi-band loop (coil) antenna 232 (represented by inductor L0), a near-field receiver circuit 260, and a far-field receiver circuit 262. The near-field receiver circuit 260 is coupled to the multi-band loop antenna 232 and is configured to generate a near-field output 250(1) comprised of near-field signals received at the multi-band loop antenna 232. The far-field receiver circuit 262 is also coupled to the multi-band loop antenna 232 and is configured to generate a far-field output 250(2) comprised of far-field signals received at the multi-band loop antenna 232. As noted, the outputs 250(1) and 250(2) are provided to implant electronics (not shown in FIG. 2) of the cochlear implant 200.

The near-field receiver circuit 260 comprises a transformer 264 with a magnetic core. The transformer 264 has a primary side (primary coil) 266 connected in series with the multi-band loop antenna 232 and a secondary side (secondary coil) 268 connected to the capacitor 270 (C1).

The far-field receiver circuit 262 comprises an isolation coupler 272. The isolation coupler 272 is connected in series with the multi-band loop antenna 232 and is connected in parallel with the transformer 264. In the embodiment of FIG. 2, the inductance of the primary side of the coupler 272, a first capacitor 274 (C2), and a second capacitor 276 (C3), which are connected between the isolation coupler 272 and the multi-band loop antenna 232, form a high-pass filter 273 for signals received at the multi-band loop antenna 232.

As noted, the receiver circuits 260 and 262 are used to receive near-field and far-field signals, respectively, via the multi-band loop antenna 232. The receiver circuits 260 and 262 operate in differential mode directly from the multi-band loop antenna 232 to receive the signals. In addition, as noted, due to the physical arrangement of the receiver circuits 260 and 262, the multi-band loop antenna 232 operates as a loop antenna to receive both the near-field and the far-field signals.

As noted above, the far-field receiver circuit 262 comprises isolation coupler 272 that is connected in series with the multi-band loop antenna 232. The isolation coupler 272 may be implemented in a number of different manners, but generally includes a first (primary) side (not shown in FIG. 2) that closes the antenna loop and a second (secondary) side (also not shown in FIG. 2) that is electrically isolated from the first side. The second side of the isolation coupler 272 generates the far-field output 250(2) that is provided to the implant electronics, while also electrically isolating the implant electronics from direct current (DC) at the primary side connected to the multi-band loop antenna 232.

As noted, in the embodiment of FIG. 2, the capacitors 274, 276, and the inductance of the primary side of the coupler 272 operate as a high-pass filter 273 that blocks the near-field signals. In addition, local ground is not required at the first side of the isolation coupler 272.

Figure 3:
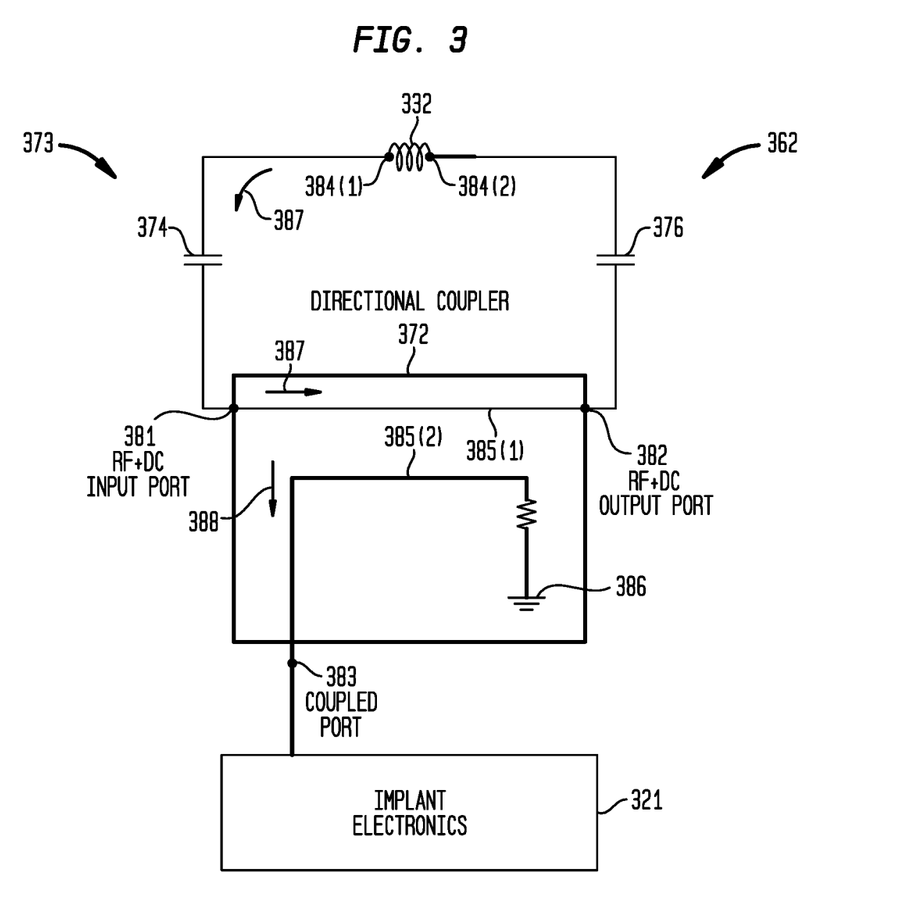
FIG. 3 is a schematic diagram illustrating a receiver circuit, in accordance with certain embodiments presented herein.

As noted, isolation coupler 272, as well other isolation couplers in accordance with embodiments presented herein, may be implemented in a number of different manners. FIG. 3 is a schematic diagram illustrating one example arrangement for isolation coupler 272, in accordance with embodiments presented herein. In this embodiment, the isolation coupler 272 is a directional coupler and is referred to herein as directional coupler 372.

Directional coupler 372 comprises an input port 381, an output port 382, and a coupled port 383. The input port 381 is connected to the positive terminal 384(1) of a multi-band loop antenna 332 via capacitor 374, while output port 382 is connected to the negative terminal 384(2) of the multi-band loop antenna 332 via capacitor 376. The capacitors 374 and 376, along with the inductance of the primary side of the coupler 372, form a high-pass filter 373 for signals received at the multi-band loop antenna 332. The multi-band loop antenna 332, capacitor 374, and capacitor 376 are substantially similar to multi-band loop antenna 232, capacitor 274, and capacitor 276, respectively, described above with reference to FIG. 2. The coupled port 383 is connected to implant electronics 321 which may be substantially similar to implant electronics 121 of FIG. 1.

As shown, the directional coupler 372 also comprises two coupled transmission lines 385(1) and 385(2). Transmission line 385(1) is connected between input port 381 and output port 382, while transmission line 385(2) is connected between coupled port 383 and an internal load 386. In certain examples, transmission line 385(1) is referred to as a "mainline" or "primary side" of the coupler 372, while transmission line 385(2) is referred to as a "coupled line" or "secondary side" of the coupler 372. Each of the transmission lines 385(1) and 385(2) have an associated inductance and can be created using a number of different technologies, such as stripline technology, microstrip technology, etc.

The transmission lines 385(1) and 385(2) are physically separated from one another and, as such, provide direct current isolation there between. However, at least a segment of each of the transmission lines 385(1) and 385(2) are positioned sufficiently close together such that energy passing through transmission line 385(1) is coupled to transmission line 385(2). That is, due to the relative positioning of the two coupled transmission lines 385(1) and 385(2), a defined amount of the electromagnetic power in transmission line 385(1) passes to transmission line 385(2) and, accordingly, to the coupled port 383 and the implant electronics 321.

In FIG. 3, arrows 387 illustrate the flow of current from multi-band loop antenna 332 through transmission line 385(1). Arrow 388 illustrates the coupled current that flows through transmission line 385(2) to coupled port 383. As shown, transmission line 385(1) closes the multi band loop antenna 332 while, due to the physical separation of the transmission lines 385(1) and 385(2), the implant electronics 321 are isolated (protected) from direct current at the multi-band loop antenna 332.

Figure 4:
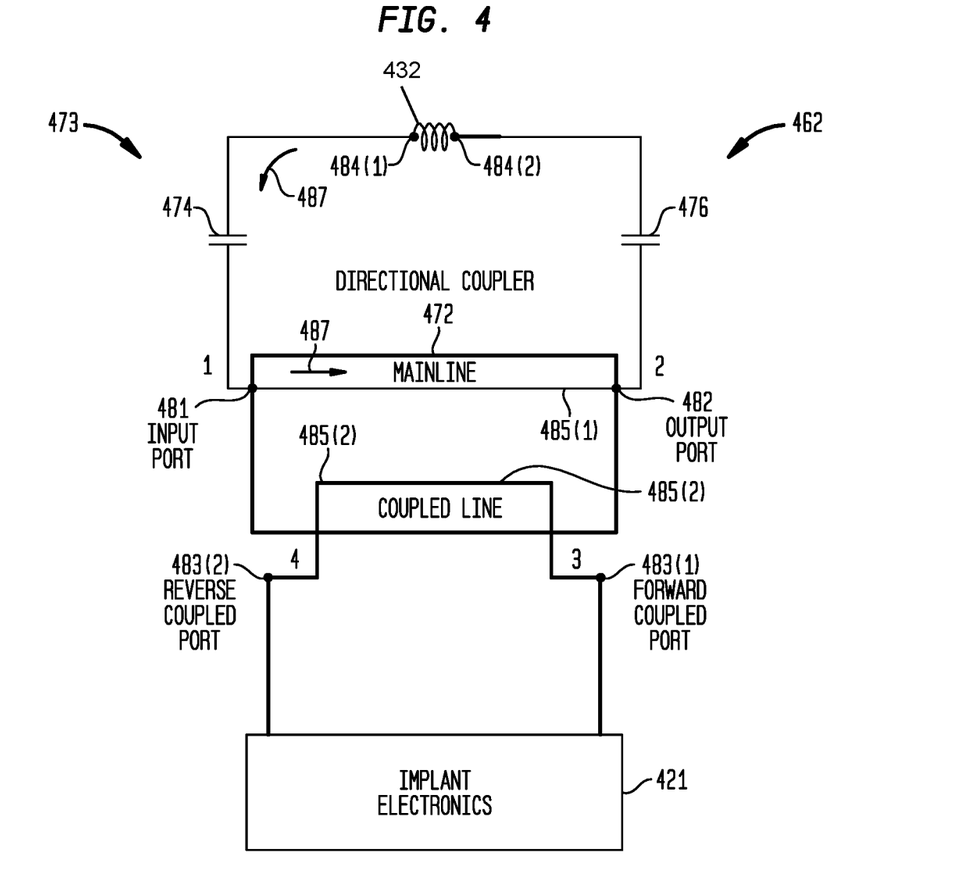
FIG. 4 is a schematic diagram illustrating another receiver circuit, in accordance with certain embodiments presented herein.

FIG. 3 is an example of a three (3) port directional coupler. It is to be appreciated that the use of a three port directional coupler is illustrative and that other directional couplers may be used in other embodiments. For example, FIG. 4 is a schematic diagram illustrating a four (4) port directional coupler 472 that can be used in accordance with embodiments presented herein. The directional coupler 472 is similar to the coupler 372 of FIG. 3 except that that both ends of the coupled line are coupled ports.

More specifically, directional coupler 472 comprises an input port 481, an output port 482, and a first coupled port 483(1) and a second coupled port 483(2). The first coupled port 483(1) is sometimes referred to herein as a "forward coupled" port, while the second coupled port 483(2) is sometimes referred to herein as a "reverse coupled" or "isolated" port. The input port 481 is connected to the positive terminal 484(1) of a multi-band loop antenna 432 via capacitor 474, while output port 482 is connected to the negative terminal 484(2) of the multi-band loop antenna 432 via capacitor 476. The capacitors 474 and 476, along with the inductance of the primary side of the coupler 472, form a high-pass filter 473 for signals received at the multi-band loop antenna 432. The multi-band loop antenna 432, capacitor 474, and capacitor 476 are substantially similar to multi-band loop antenna 232, capacitor 274, and capacitor 276, respectively, described above with reference to FIG. 2. The coupled ports 483(1) and 483(2) are connected to implant electronics 421, which may be substantially similar to implant electronics 121 of FIG. 1. In certain examples, the reverse coupled port 483(2) may be terminated with an external load (not shown in FIG. 4)

As shown, the directional coupler 472 also comprises two coupled transmission lines 485(1) and 485(2) that form the primary and secondary sides, respectively, of the coupler 472. Transmission line 485(1) is connected between input port 481 and output port 482, while transmission line 485(2) is connected between coupled ports 483(1) and 483(2). Similar to the above embodiments, the transmission lines 485(1) and 485(2) can be created using a number of different technologies (e.g., stripline technology, microstrip technology, etc.).

The transmission lines 485(1) and 485(2) are physically separated from one another. However, at least a segment of each of the transmission lines 485(1) and 485(2) are positioned sufficiently close together such that energy passing through transmission line 485(1) is coupled to transmission line 485(2). That is, due to the relative positioning of the two coupled transmission lines 485(1) and 485(2), a defined amount of the electromagnetic power in transmission line 485(1) passes to transmission line 485(2) and, accordingly, to the forward coupled port 483(1) and the implant electronics 421.

In FIG. 4, arrows 487 illustrate the flow of current from multi-band loop antenna 432 through transmission line 485(1). Arrow 488 illustrates the induced (coupled) current that flows through transmission line 485(2) to forward coupled port 483(1). As shown, transmission line 485(1) closes the multi band loop antenna 432 while, due to the physical separation of the transmission lines 485(1) and 485(2), the implant electronics 421 are isolated (protected) from direct current at the multi-band loop antenna 432.

FIGS. 3 and 4 illustrate example arrangements for isolation couplers in accordance with embodiments presented herein. In the example arrangements of FIGS. 3 and 4, the coupling is via two transmission lines. In further embodiments, the transmission lines may be replaced by coils so as to form an air transformer (i.e., a transformer without a magnetic core). In certain embodiments, an isolation coupler may be implemented as a balun operating as an air transformer.

Figure 5:
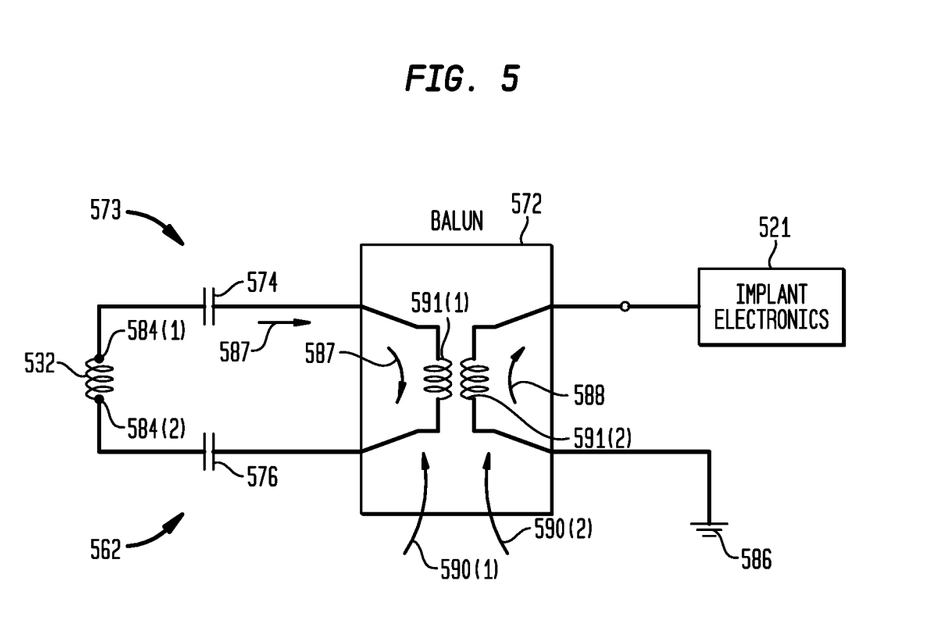
FIG. 5 is a schematic diagram illustrating another receiver circuit, in accordance with certain embodiments presented herein.

For example, FIG. 5 is a simplified schematic diagram illustrating one arrangement for far-field receiver circuit 262, referred to as far-field receiver circuit 562, in which the isolation coupler is formed by a balun 572. In this example, the balun 572 operates as an air transformer or directional coupler and comprises a primary side 590(1) and a secondary side 590(2). The primary and secondary sides 590(1) and 590(2) include coils 591(1) and 591(2), respectively.

The primary side 590(1) of the balun 572 is connected between positive terminal 584(1) of a multi-band loop antenna 532 via capacitor 574 and the negative terminal 584(2) of the multi-band loop antenna 532 via capacitor 576. The capacitors 574 and 576, along with the inductance of the primary side of the coupler 572, form a high-pass filter 573 for signals received at the multi-band loop antenna 432. The multi-band loop antenna 532, capacitor 574, and capacitor 576 are substantially similar to multi-band loop antenna 232, capacitor 274, and capacitor 276, respectively, described above with reference to FIG. 2. The secondary side 590(2) of the balun 572 is connected between a load 586 and implant electronics 521, which may be substantially similar to implant electronics 121 of FIG. 1.

The coils 591(1) and 591(2) are physically separated from one another but are positioned sufficiently close together such that energy passing through coil 591(1) is coupled to coil 591(2) and, as such, a defined amount of the electromagnetic power in 591(1) passes to 591(2) and the implant electronics 521. In certain examples, some inductance and capacitance may be added in line with the coils 591(1) and 591(2) to balance the output. For ease of illustration, such additional inductance and capacitance have been omitted from FIG. 5.

In FIG. 5, arrows 587 illustrate the flow of current from multi-band loop antenna 532 through coil 591(1). Arrow 588 illustrates the induced (coupled) current that flows through coil 591(2). As shown, coil 591(1) closes the multi band loop antenna 532 while, due to the physical separation of the coils 591(1) and 591(2)2), the implant electronics 521 are isolated (protected) from the multi-band loop antenna 432. That is, balun 572 isolates the implant electronics 521 from direct current at the multi-band loop antenna 532.

Although embodiments have been primarily described with reference to cochlear implants, it is to be appreciated that the techniques presented herein may be implemented in other implantable medical devices, such as other types of auditory prostheses.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device, comprising:
    a multi-band loop antenna;
    implant electronics;
    a near-field receiver circuit coupled to the loop antenna and the implant electronics and configured to receive, via the loop antenna, near-field signals from one or more devices positioned external to a body of a recipient and to provide the near-field signals to the implant electronics; and
    a far-field receiver circuit coupled to the loop antenna and the implant electronics and configured to receive, via the loop antenna, far-field signals from at least one device positioned external to the body of the recipient and to provide the far-field signals to the implant electronics, and
    wherein the far-field receiver circuit is configured to electrically isolate the implant electronics from direct current at the multi-band loop antenna.

2. The implantable medical device of claim 1, wherein the near-field receiver circuit comprises a transformer and the far-field receiver circuit comprises an isolation coupler.

3. The implantable medical device of claim 2, wherein the transformer and the isolation coupler are connected in parallel with one another.

4. The implantable medical device of claim 2, wherein the isolation coupler is a directional coupler comprising:
    a first transmission line having first and second ends connected to first and second terminals, respectively, of the multi-band loop antenna; and
    a second transmission line physically separated from the first transmission line having at least a first end connected to the implant electronics.

5. The implantable medical device of claim 4, further comprising:
    a first capacitor connected between the first end of the first transmission line and the first terminal of the multi-band loop antenna; and
    a second capacitor connected between the second end of the first transmission line and the second terminal of the multi-band loop antenna,
    wherein an inductance of the first transmission line, the first capacitor, and the second capacitor collectively form a high-pass filter.

6. The implantable medical device of claim 4, wherein a second end of the second transmission line is connected to an internal load.

7. The implantable medical device of claim 2, wherein the isolation coupler comprises a balun.

8. The implantable medical device of claim 1, wherein the implantable medical device is a cochlear implant.

9. The implantable medical device of claim 1, wherein the near-field receiver circuit and the far-field receiver circuit are configured to operate in differential mode directly from the multi-band loop antenna to receive both the near-field signals and the far-field signals, respectively.

10. An implantable medical device, comprising:
    implant electronics;
    an implantable loop antenna;
    a transformer having a primary side connected to the loop antenna and a secondary side connected to the implant electronics, wherein the transformer is configured to receive, via the loop antenna, radio-frequency (RF) signals in a near-field; and
    an isolation coupler having a primary side connected to the implantable loop antenna and a second side connected to the implant electronics, wherein the isolation coupler is configured to receive, via the loop antenna, RF signals in a far-field,
    wherein the transformer and the isolation coupler are connected in parallel with one another.

11. The implantable medical device of claim 10, further comprising:

first and second capacitors connected in series with the primary side of the isolation coupler and are disposed on opposing sides of the primary side of the isolation coupler, and wherein an inductance of the primary side of the isolation coupler, the first capacitor, and the second capacitor operate as a high-pass filter.

12. The implantable medical device of claim 10, wherein the isolation coupler comprises a directional coupler having a first transmission line forming the primary side of the isolation coupler and a second transmission line forming the secondary side of the isolation coupler, wherein the second transmission line is physically separated from the first transmission line.

13. The implantable medical device of claim 12, wherein a first end of the second transmission line is connected to the implant electronics and a second end of the second transmission line is connected to an internal load of the isolation coupler.

14. The implantable medical device of claim 10, wherein the isolation coupler is formed by a balun.

15. The implantable medical device of claim 10, wherein the isolation coupler is configured to electrically isolate the implant electronics from direct current at the loop antenna.

16. An implantable medical device, comprising:
  implant electronics;
  an implantable loop antenna configured to receive both near-field radio-frequency (RF) signals and far-field RF signals from one or more devices positioned external to a body of a recipient;
  a transformer disposed between the implant electronics and the loop antenna and configured to provide the near-field RF signals to the implant electronics;
  an isolation coupler disposed between the implant electronics and the loop antenna and configured to provide the far-field RF signals to the implant electronics; and
  first and second capacitors connected in series with a primary side of the isolation coupler, and wherein the first and second capacitors are disposed on opposing sides of the primary side of the isolation coupler.

17. The implantable medical device of claim 16, wherein the isolation coupler comprises a directional coupler having a first transmission line and a second transmission line that is physically separated from the first transmission line.

18. The implantable medical device of claim 17, wherein the first transmission line comprises first and second ends, and wherein:
  the first capacitor is connected between the first end of the first transmission line and a first terminal of the loop antenna; and
  the second capacitor is connected between the first end of the first transmission line and the first terminal of the loop antenna.

19. The implantable medical device of claim 17, wherein a first end of the second transmission line is connected to the implant electronics and a second end of the second transmission line is connected to an internal load of the isolation coupler.

20. The implantable medical device of claim 16, wherein the isolation coupler is configured to electrically isolate the implant electronics from direct current at the loop antenna.

21. The implantable medical device of claim 16, wherein the isolation coupler is formed by a balun.

22. An implantable medical device, comprising:
  a loop antenna;
  a near-field receiver circuit coupled to the loop antenna and configured to receive, via the loop antenna, near-field signals from one or more devices positioned external to a body of a recipient;
  a far-field receiver circuit coupled to the loop antenna and configured to receive, via the loop antenna, far-field signals from at least one device positioned external to the body of the recipient; and
  implant electronics coupled to both the near-field receiver circuit and the far-field receiver circuit, wherein the far-field receiver circuit is configured to electrically isolate the implant electronics from direct current at the loop antenna, and wherein the near-field receiver circuit and the far-field receiver circuit are configured to operate in differential mode directly from the loop antenna to receive both the near-field signals and the far-field signals, respectively.

23. The implantable medical device of claim 22, wherein the near-field receiver circuit comprises a transformer and the far-field receiver circuit comprises an isolation coupler.

24. The implantable medical device of claim 23, wherein the transformer and the isolation coupler are connected in parallel with one another.

25. The implantable medical device of claim 23, wherein the isolation coupler is a directional coupler comprising:
  a first transmission line having first and second ends connected to first and second terminals, respectively, of the loop antenna; and
  a second transmission line physically separated from the first transmission line having at least a first end connected to implant electronics.

26. The implantable medical device of claim 25, further comprising:
  a first capacitor connected between the first end of the first transmission line and the first terminal of the loop antenna; and
  a second capacitor connected between the second end of the first transmission line and the second terminal of the loop antenna,
  wherein an inductance of the first transmission line, the first capacitor, and the second capacitor collectively form a high-pass filter.

27. The implantable medical device of claim 25, wherein a second end of the second transmission line is connected to an internal load.

* * * * *

UNITED STATES PATENT AND TRADEMARK OFFICE
CERTIFICATE OF CORRECTION

| | | |
|---|---|---|
| PATENT NO. | : 10,658,745 B2 | Page 1 of 1 |
| APPLICATION NO. | : 15/697618 | |
| DATED | : May 19, 2020 | |
| INVENTOR(S) | : Guilhem Vavelin and Gauthier Jodin | |

It is certified that error appears in the above-identified patent and that said Letters Patent is hereby corrected as shown below:

In the Specification

Column 6, Line 39, remove "with" and insert --without--

Column 6, Line 39, insert --(i.e., an air transformer)-- after "a magnetic core"

Signed and Sealed this
Fourth Day of August, 2020

Andrei Iancu
*Director of the United States Patent and Trademark Office*